United States Patent
Hsieh et al.

(10) Patent No.: US 8,971,605 B2
(45) Date of Patent: Mar. 3, 2015

(54) SYSTEM AND METHOD FOR CORRECTING FOR METAL ARTIFACTS USING MULTI-ENERGY COMPUTED TOMOGRAPHY

(75) Inventors: Jiang Hsieh, Brookfield, WI (US); Brian Edward Nett, Madison, WI (US); Paavana Sainath, Oconomowoc, WI (US); Debashish Pal, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 251 days.

(21) Appl. No.: 13/593,348

(22) Filed: Aug. 23, 2012

(65) Prior Publication Data
US 2014/0056497 A1    Feb. 27, 2014

(51) Int. Cl.
*G06K 9/00* (2006.01)
*A61B 6/00* (2006.01)

(52) U.S. Cl.
USPC .................. 382/131; 378/4; 378/21

(58) Field of Classification Search
CPC .................................. G06K 9/00; G06T 1/00
USPC ......... 382/128, 129, 130, 131, 132, 133, 134; 378/2, 4, 8, 21–27, 62, 101, 901; 600/404, 410, 411, 425, 427; 128/92, 128/922
See application file for complete search history.

(56) References Cited

U.S. PATENT DOCUMENTS 6,574,304 B1 *   6/2003   Hsieh et al. .................. 378/62
8,503,750 B2 *   8/2013   Benson et al. ............... 382/131

* cited by examiner

*Primary Examiner* — Abolfazl Tabatabai
(74) *Attorney, Agent, or Firm* — Fletcher Yoder, P.C.

(57) ABSTRACT

A method is provided. The method includes acquiring a first dataset at a first energy spectrum and a second dataset at a second energy spectrum. The method also includes extracting a metal artifact correction signal using the first dataset and the second dataset or using a first reconstructed image and a second reconstructed image generated respectively from the first and the second datasets. The method further includes performing metal artifact correction on the first reconstructed image using the metal artifact correction signal to generate a first corrected image.

22 Claims, 3 Drawing Sheets

SYSTEM AND METHOD FOR CORRECTING FOR METAL ARTIFACTS USING MULTI-ENERGY COMPUTED TOMOGRAPHY

BACKGROUND

Non-invasive imaging technologies allow images of the internal structures or features of a patient to be obtained without performing an invasive procedure on the patient. In particular, such non-invasive imaging technologies rely on various physical principles, such as the differential transmission of X-rays through the target volume or the reflection of acoustic waves, to acquire data and to construct images or otherwise represent the observed internal features of the patient.

For example, in computed tomography (CT) and other X-ray based imaging technologies, X-ray radiation spans a subject of interest, such as a human patient, and a portion of the radiation impacts a detector where the image data is collected. In digital X-ray systems a photodetector produces signals representative of the amount or intensity of radiation impacting discrete pixel regions of a detector surface. The signals may then be processed to generate an image that may be displayed for review. In CT systems a detector array, including a series of detector elements, produces similar signals through various positions as a gantry is displaced around a patient.

In the images produced by such systems, it may be possible to identify and examine the internal structures and organs within a patient's body. However, the produced images may also include artifacts such as metal artifacts that adversely affect the quality of the images due to a variety of factors. In conventional computed tomography (CT), these metal artifacts are difficult to remove from the images.

BRIEF DESCRIPTION

In accordance with a first embodiment, a method is provided. The method includes acquiring a first dataset at a first energy spectrum and a second dataset at a second energy spectrum. The method also includes extracting a metal artifact correction signal using the first dataset and the second dataset or using a first reconstructed image and a second reconstructed image generated respectively from the first dataset and the second dataset. The method further includes performing metal artifact correction on the first reconstructed image using the metal artifact correction signal to generate a first corrected image.

In accordance with a second embodiment, one or more non-transitory computer-readable media are provided. The computer-readable media encode one or more processor-executable routines. The one or more routines, when executed by a processor, cause acts to be performed including: acquiring a first dataset at a first energy spectrum and a second dataset at a second energy spectrum, extracting a metal artifact correction signal using the first dataset and the second dataset or using a first reconstructed image and a second reconstructed image generated respectively from the first dataset and the second dataset, and performing metal artifact correction on the first reconstructed image using the metal artifact correction signal to generate a first corrected image.

In accordance with a third embodiment, a system is provided. The system includes a memory structure encoding one or more processor-executable routines. The routines, when executed, cause acts to be performed including: acquiring a first dataset at a first energy spectrum and a second dataset at a second energy spectrum, extracting a metal artifact correction signal using the first dataset and the second dataset or using a first reconstructed image and a second reconstructed image generated respectively from the first dataset and the second dataset, and performing metal artifact correction on the first reconstructed image using the metal artifact correction signal to generate a first corrected image. The system also includes a processing component configured to access and execute the one or more routines encoded by the memory structure.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
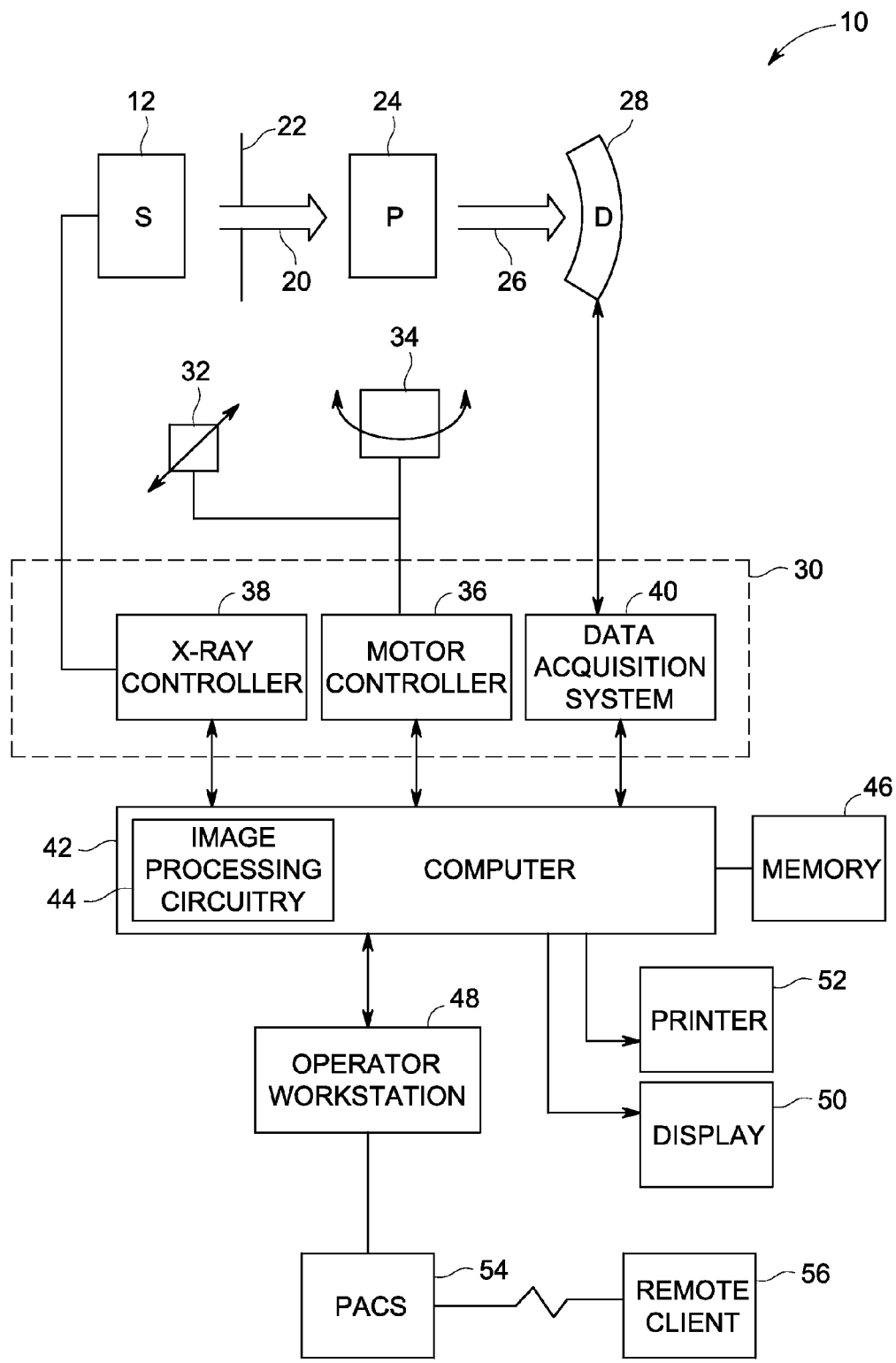
FIG. 1 is a schematic illustration of an embodiment of a computed tomography (CT) system configured to acquire CT images of a patient and to process the images in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

Tissue characterization or classification may be desirable in various clinical contexts to assess the tissue being characterized for pathological conditions and/or to assess the tissue for the presence of various elements, chemicals or molecules of interest. However, tissue characterization in imaging studies, such as using computed tomography (CT), may be problematic due to the presence of metal artifacts (i.e., artifacts in the images attributable to metal within the imaged volume) present within the reconstructed images. As discussed herein, in various implementations, a multi-energy CT approach is employed to compensate for the metal artifacts within the reconstructed images.

In particular, as described herein, a projection-space correction approach is used to compensate for the metal artifacts. The approach utilizes datasets or a set of images at two different energy spectrums derived from the original dual energy scans. The severity of artifacts from a scanned metal object within the reconstructed images changes with different X-ray tube voltages. However, the appearance or signature of the artifacts within the reconstructed images is similar regardless of the X-ray spectrum. The projection-space correction approach takes advantage of the similar or common artifact signatures to extract a metal artifact correction signal for correcting the original reconstructed images via image processing manipulations, while minimizing the impact on residual signals from normal anatomies such as the soft tissue and bones. It should be pointed out that the selection of the energy spectrum pair is significantly different from the conventional dual energy scans in CT systems. In conventional dual-energy scans, one of the important criteria is to make sure that the two energy spectrums are as different as possible. To this aim, typical dual-energy scans utilize 80 kVp and 140 kVp scans, since these two settings represent the most different energy spectrums available on the scanner. The selection of the two energy spectrums for metal artifact reduction, however, is just the opposite. We want to select an energy spectrum pair that represent as "hard" of x-ray beams as possible. On a typical CT system, this can be accomplished by using 120 kVp and 140 kVp settings. By selecting "harder" x-ray beams, we avoid many issues associated with metal artifacts, such as x-ray photon starvation and severe beam-hardening. Since 120 kVp and 140 kVp spectrums are different, they should still provide useful information to extract metal artifact signals. To accomplish the goal outlined above, one could further employ additional filtrations in the data collection. For example, additional tin, copper, or other pre-patient filters can be used to further "harden" the x-ray beams at both 120 kVp and 140 kVp settings. Of course, the type and amount of filtration can be different during the data collection of two datasets. Alternatively, higher kVp settings can be utilized to accomplish similar goal. For example, 150 kVp or 160 kVp (which are not available on typical CT scanners) can be used to perform data collection. For example, the projection-space correction approach may be used for highly attenuating metals (e.g., stainless steel) that generate artifacts. In addition, the projection-space correction approach takes into account the difference in Hounsfield units (HU) of the images across different X-ray tube voltages, the selection of data to be used for generating the artifact signature, and motion.

With the foregoing discussion in mind, FIG. 1 illustrates an embodiment of an imaging system 10 for acquiring and processing image data in accordance with aspects of the present disclosure. In the illustrated embodiment, system 10 is a computed tomography (CT) system designed to acquire X-ray projection data, to reconstruct the projection data into a tomographic image, and to process the image data for display and analysis. The CT imaging system 10 includes an X-ray source 12. As discussed in detail herein, the source 12 may include one or more X-ray sources, such as an X-ray tube or solid state emission structures. The X-ray source 12, in accordance with present embodiments, is configured to emit an X-ray beam 20 at one or more energies. For example, the X-ray source 12 may be configured to switch between relatively low energy polychromatic emission spectra (e.g., at about 80 kVp) and relatively high energy polychromatic emission spectra (e.g., at about 140 kVp). As will be appreciated, the X-ray source 12 may also be operated so as to emit X-rays at more than two different energies, though dual-energy embodiments are discussed herein to simplify explanation. Similarly, the X-ray source 12 may emit at polychromatic spectra localized around energy levels (i.e., kVp ranges) other than those listed herein (e.g., 100 kVP, 120 kVP, etc.). Indeed, selection of the respective energy levels for emission may be based, at least in part, on the anatomy being imaged.

In certain implementations, the source 12 may be positioned proximate to a collimator 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements. Each detector element produces an electrical signal that represents the intensity of the X-ray beam incident at the position of the detector element when the beam strikes the detector 28. Electrical signals are acquired and processed to generate one or more scan datasets.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28 in accordance with the steps and processes discussed herein. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. In addition, in some embodiments the X-ray controller 38 may be configured to selectively activate the source 12 such that tubes or emitters at different locations within the system 10 may be operated in synchrony with one another or independent of one another. In certain embodiments discussed herein, the X-ray controller 38 may be configured to provide fast-kVp switching of the X-ray source 12 so as to rapidly switch the source 12 to emit X-rays at the respective polychromatic energy spectra in succession during an image acquisition session. For example, in a dual-energy imaging context, the X-ray controller 38 may operate the X-ray source 12 so that the X-ray source 12 alternately emits X-rays at the two polychromatic energy spectra of interest, such that adjacent projections are acquired at different energies (i.e., a first projection is acquired at high energy, the second projection is acquired at low energy, the third projection is acquired at high energy, and so forth). In one such implementation, the fast-kVp switching operation performed by the X-ray controller 38 yields temporally registered projection data. In some embodiments, other modes of data acquisition and processing may be utilized. For example, a low pitch helical mode, rotate-rotate axial mode, N×M mode (e.g., N low-kVp views and M high-kVP views) may be utilized to acquire dual-energy datasets.

As noted above, the X-ray source 12 may be configured to emit X-rays at more than one energy spectrum. That is, though such emissions may be generally described or discussed as being at a particular energy (e.g., 80 kVp, 140 kVp, and so forth), the respective X-ray emissions at a given energy are actually along a continuum or spectrum and may, therefore, constitute a polychromatic emission centered at, or having a peak strength at, the target energy. It should be noted in certain embodiments, global X-ray spectral imaging may be utilized to generate monochromatic images at different energy levels.

The system controller 30 may include a data acquisition system (DAS) 40. The DAS 40 receives data collected by readout electronics of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer 42 may include or communicate with one or more non-transitory memory devices 46 that can store data processed by the computer 42, data to be processed by the computer 42, or instructions to be executed by a processor 44 of the computer 42. For example, a processor of the computer 42 may execute one or more sets of instructions stored on the memory 46, which may be a memory of the computer 42, a memory of the processor, firmware, or a similar instantiation. In accordance with present embodiments, the memory 46 stores sets of instructions that, when executed by the processor, perform image processing methods as discussed herein (e.g., extraction of a metal artifact correction signal and performance of metal artifact correction).

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, contrast agent density maps produced in accordance with the present disclosure, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Figure 2:
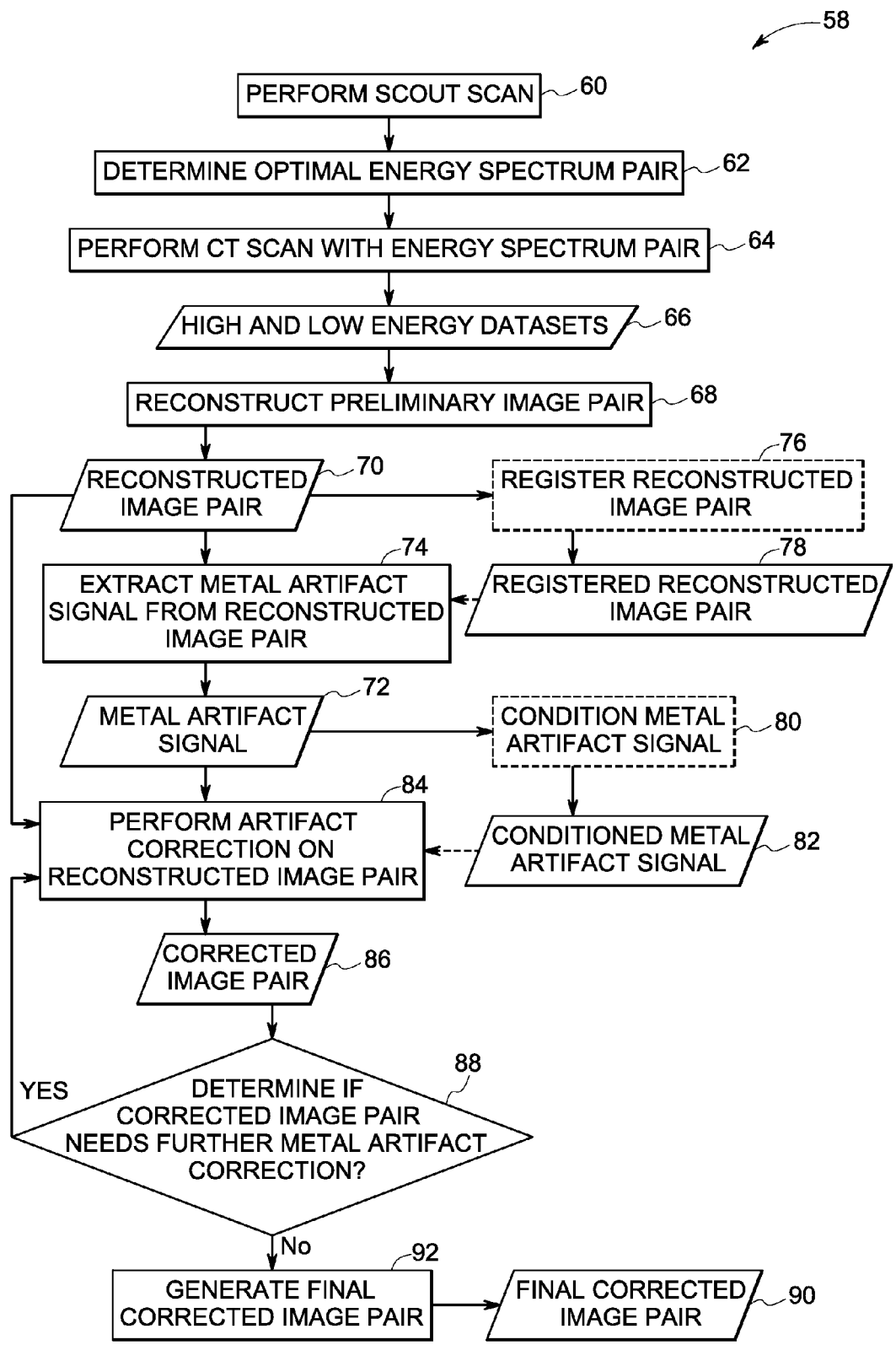
FIG. 2 is a process flow diagram of an embodiment of a method for performing metal artifact correction on images.

Keeping in mind the operation of the system 10 and, specifically, the X-ray source 12 discussed above with respect to FIG. 1, FIG. 2 illustrates a process flow diagram of an embodiment of a method 58 for performing metal artifact correction on images. Any suitable application-specific or general-purpose computer having a memory and processor may perform some or all of the steps of the method 58. By way of example, as noted above with respect to FIG. 1, the computer 42 and associated memory 46 may be configured to perform the method 58. For example, the memory 46, which may be any tangible, non-transitory, machine-readable medium (e.g., an optical disc, solid state device, chip, firmware), may store one or more sets of instructions that are executable by a processor of the computer 42 to perform the steps of method 58. In accordance with present embodiments, the processor, in performing method 58, may generate one or more images corrected for metal artifacts.

In the depicted implementation, the method 58 includes performing a scout scan (block 60) on the subject using the system 10. A scout scan refers to all data acquisitions wherein the gantry is stationary and the table is moved. During the scout scan, the subject is scanned with a very low dose and attenuation measurements are obtained along the length of the subject. The scout scan generates a planar 2D image of the subject. The scout scan enables a determination of the size of the scanned object (e.g., metal object) and the level of attenuation caused by the scanned object. The method 58 includes determining the optimal voltage pair (e.g., optimal energy spectra) for data acquisition (block 62). For example, in certain embodiments, if the scout scan indicates that the scanned object is not exceedingly large and the metal objects are not exceedingly attenuating, 100 kVp and 140 kVp may be selected as the optimal voltage pair. In other embodiments, other voltage pairs may be utilized (e.g., 120 kVP and 140 kVp). In certain embodiments, the voltage pair may be selected without utilizing a scout scan. For example, the two highest kVP settings may be selected (e.g., 120 kVP and 140 kVp). Alternatively, prior information obtained from patients can also be used to determine the optimal energy spectrum pair. For example, when performing neural scans, it is unlikely that large size of stainless steel will be present inside the FOV. In such cases, 100 kVp and 140 kVp can be selected as the pair, or 120 kVp and 140 kVp are selected without additional filtration. On the other hand, when a pelvis scan is performed and the patient is known to have a metal implant, 130 kVp and 150 kVp can be selected, or 120 kVp and 140 kVp may be used in combination with additional filtration.

Upon determining the optimal voltage pair or energy spectrum pair (block 62), the method 58 includes performing a CT scan with the selected voltage pair (block 64) to acquire an image or set of images 66 (e.g., high and low energy datasets) for each selected voltage (e.g., energy spectrum) of the voltage pair. The data collection mode can be fast-kVp switching (as described before), rotate-rotate scans, or slow-switching helical scans. In the rotate-rotate mode, the patient table remains stationary while two energy scans are collected sequentially. This can be either two half-scans or two full-scans. In the slow-switching helical scans, low-pitch helical (e.g., 0.5:1 pitch) is used and the X-ray spectrum is changed either over a half-scan range (180 degree plus fan-angle) or full-scan range (360 degree), or somewhere in between. The description throughout references obtaining images (e.g., polychromatic images) at different energy spectrums. However, in certain embodiments (e.g., using global X-ray spectral imaging), monochromatic images may be generated at different energy levels (e.g., keV) and the desired monochromatic images at two different keV levels may be selected from among these images to use in the metal artifact correction processing. The pair of monochromatic images may be selected based on obtaining an accurate metal artifact signature without adversely impacting the differential signals for the different anatomies and/or contrast agents. Monochromatic images have different HU values as a function of energy. Thus, in embodiments where monochromatic images are selected for use in the metal artifact correction processing, scaling may be performed on the images for water since the HU value for water is known for different energies.

The method 58 further includes reconstructing a preliminary image or image set 70 (e.g., first-pass reconstruction) for the high and low energy images 66 associated with each selected spectrum of the spectrum pair (block 68). It should be pointed out that "spectrum" and "spectrum pair" are not limited to the change of x-ray generator voltage supplied to the x-ray tube, they can be modifications to the pre-patient filtration or the combination of filtration with voltage change, as discussed previously. For example, a reconstructed image or set of images may be generated for a first image or set of images at a first energy spectrum (e.g., 120 kVp) and a reconstructed image or set of images may be generated for a second image or set of images generated at a second energy spectrum (e.g., 140 kVp). The images 66 associated with block 68 may be obtained at the time of imaging the subject 24 or post-imaging. For example, obtaining the images 66 may include executing an imaging protocol using the system 10 of FIG. 1 to generate the images 66 as described above with respect to block 64. Alternatively or additionally, the acts associated with block 68 may include accessing the images 66 from memory, such as from a local storage device or from an image archiving system, such as the PACS 54 of FIG. 1. Therefore, the acts associated with block 68 may be performed by the system 10, or by a computing device local to or remote from the facility in which the image is acquired.

Upon generating the reconstructed images 70 (block 68), the method 58 includes extracting a differential signal for the metal artifact (e.g., metal artifact signal 72) from the pair of reconstructed images 70 or reconstructed images sets for the selected voltage pair (block 74). In certain embodiments, the high and low energy datasets 66 may be utilized instead of the reconstructed images 70 in extracting the metal artifact signal (block 72) and subsequent acts in the metal artifact processing. The metal artifact signal 72, $\delta(x, y, z)$, may be generated by subtraction of the two first-pass reconstructed images 70, $f(x, y, z)$ and $g(x, y, z)$ or the two scans (e.g., images 66), where f represents an image obtained at a first energy spectrum and g represents an image obtained at a second energy spectrum. Alternatively, the metal artifact signal may be obtained via summation of polynomial functions (or other functions) of the two datasets or reconstructed image sets as in the following equation:

$$\delta(x,y,z) = \Sigma_{k=0}^{N} \alpha_k f^{N-k}(x,y,z) g^k(x,y,z) \quad (1),$$

where $\alpha$ represents an experimentally determined parameter.

Motion may cause misregistration between the images 70 used to extract the metal artifact signal 72. Thus, in certain embodiments, prior to extracting the metal artifact signal 72, the method 58 includes registering the pair of datasets 66 or reconstructed images sets 70 for the pair of voltages to each other (block 76) to generate a registered pair of datasets or reconstructed image sets 78. These registered pair of datasets or reconstructed image sets 78 may be used instead in the acts of block 74 to extract the metal artifact signal 72 to improve artifact reduction and to improve the shape of the metal after correction.

Figure 3:
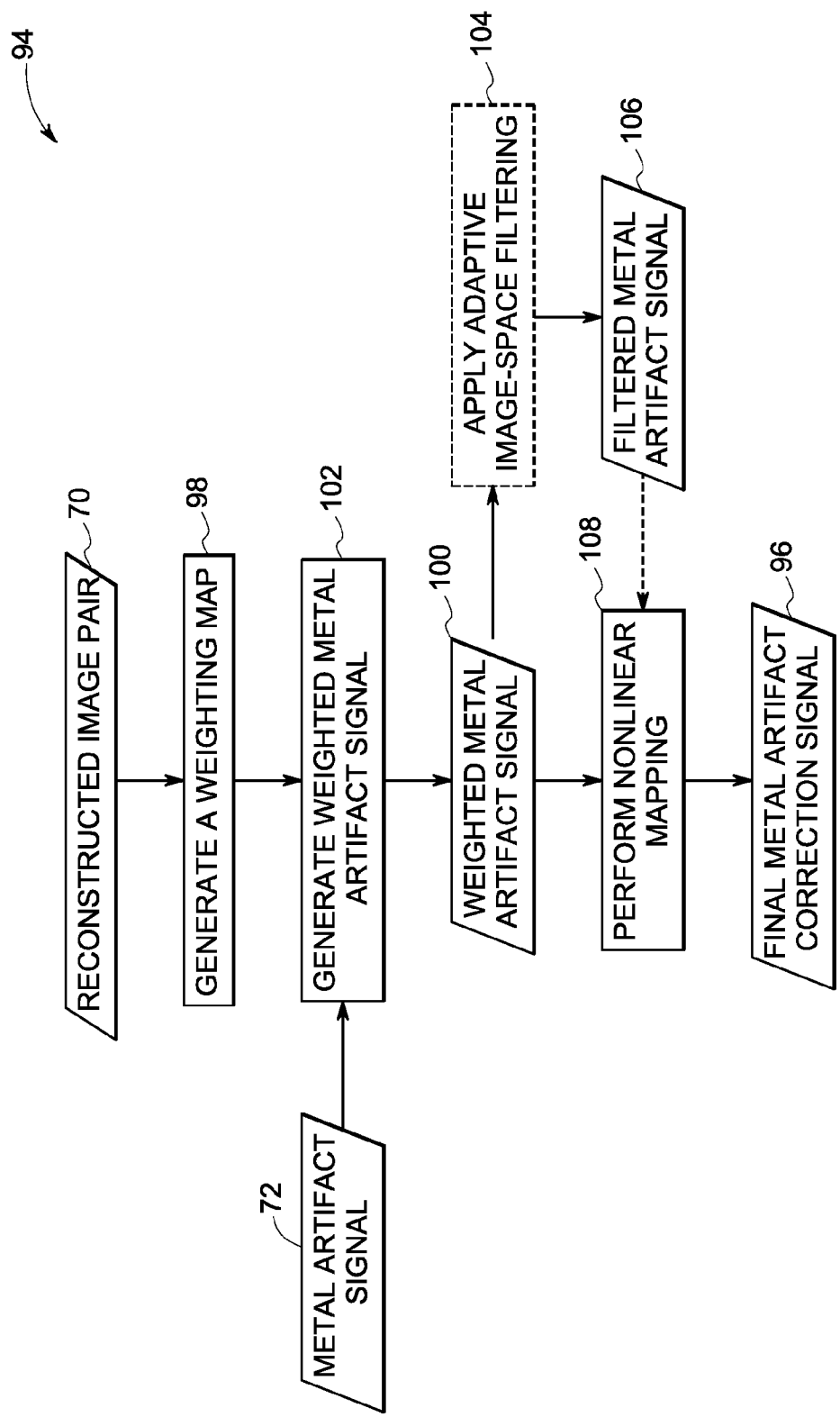
FIG. 3 is a process flow diagram of an embodiment of a method for conditioning a metal artifact signal.

In certain embodiments, the extracted metal artifact signal 72 may be conditioned (block 80) to generate a conditioned metal artifact signal 82 via a variety of techniques as described in greater detail in FIG. 3. The method 58 includes using the metal artifact signal 72 or conditioned metal artifact signal 82 as the final metal artifact correction signal, $\epsilon(x, y, z)$, to perform metal artifact correction on the pair of reconstructed images 70 or reconstructed image sets (block 84) to generate a pair of corrected images 86 or images sets for each pair of voltages. In another embodiment, the extracted metal signal from the datasets (not the reconstructed images) may undergo polynomial mapping or other mapping functions, prior to the image reconstruction process to produce metal artifact signal from the dataset produced metal signal. It is well known that the metal artifact production is a nonlinear process, and remapping the differential metal projection signal by a nonlinear process will mimic the true metal artifact production, given the tomographic reconstruction process is linear.

In certain embodiments, metal artifact construction may be performed on only a single reconstructed image 70 or reconstructed image set for one voltage of the pair of voltages. The resulting corrected images 86 or image sets, f'(x, y, z) and g'(x, y, z), where f' represents a corrected image 86 or image set for a first energy spectrum and g' represents a corrected image 86 or image set for a second energy spectrum, may be obtained via the following equations:

$$f'(x,y,z) = f(x,y,z) - \beta \cdot \epsilon(x,y,z) \quad (2)$$

and $$g'(x,y,z) = g(x,y,z) - \gamma \cdot \epsilon(x,y,z) \quad (3)$$

where $\beta$ and $\gamma$ represent experimentally determined parameters. In certain embodiments, the parameters $\beta$ and $\gamma$ may be automatically determined for each image set. The experimentally determined parameters enable the minimization of an objective function that provides an artifact measure such as the total variation, variance in the images or the entropy. Thus, in an image where the streak content from the metal artifacts is isolated, the metal artifact correction signal, $\epsilon(x, y, z)$ provides maximum artifact reduction when combined with the original images 66, 70. In some embodiments, additional processing steps may be applied to the corrected images to further improve image quality. For example, iterative beam-hardening correction may be utilized.

Upon obtaining the corrected images 86 or sets of corrected images, the method 58 includes determining if the corrected images 86 or sets of corrected images need further artifact correction (block 88). If the corrected images 86 or sets of corrected images do not need further metal artifact correction, then final corrected images or sets of final corrected images 90 are generated (block 92). However, if the corrected images 86 or sets of corrected images need further metal artifact correction, then metal artifact correction is performed again (block 84) iteratively until no further metal artifact correction is needed (or certain predetermined criteria are met) and the final corrected images 90 are generated. The determination of whether the corrected images 86 need further artifact correction (block 88) may utilize a variety of techniques. For example, the brightness within a region of interest near the metal and a region of interest away from the metal may be compared within the corrected image 86. In another embodiment, the delta, $\Delta$, or average change between different iterations of corrected images 86 may be compared until the delta is minimal or meets a certain threshold.

As described above, the metal artifact signal 72 may be conditioned to generate a conditioned metal artifact signal 82 or final metal artifact correction signal 96. FIG. 3 illustrates a method 94 for conditioning the metal artifact signal 72. Based on the first-pass reconstruction of the reconstructed images 70 or reconstructed images sets for each voltage, the locations and sizes of the metal objects may be determined. Due to the characteristics of the reconstruction algorithm (e.g., filtered back projection reconstruction algorithm), the impact of a metal-induced error falls off as 1/r, wherein r represents the distance from the source of error. Based on this, the method 94 includes generating a weighting map, w(r), to determine an amount of correction to use with the original metal artifact correction signal 72, δ(x, y, z), in correcting the reconstructed images 70 or reconstructed image sets for either or both of the voltages (block 98). The method 94 further includes weighting the metal artifact correction signal 72 with the weighting map to generate a weighted metal artifact correction signal 100, ρ(x, y, z) (block 102), as described in the following equation:

$$\rho(x,y,z)=w(x,y,z)\delta(x,y,z) \quad (4).$$

The weighted metal artifact correction signal 100 may include more noise than either f(x, y, z) or g(x, y, z). Thus, in certain embodiments, the method 94 includes applying adaptive image-space filtering to the weighted metal artifact correction signal 100 (block 104) to suppress or reduce the noise and generate a filtered metal artifact signal 106. For example, an anisotropic diffusion filter may be applied to the weighted metal artifact correction signal to suppress noise in the signal.

The method 94 further includes performing a nonlinear mapping operation on the weighted metal artifact correction signal 100 or filtered metal artifact signal 106 to enhance or suppress certain signals (block 108). The metal artifact correction signal 100 may produce shading artifacts that represent a compressed version of the true artifacts present in the original images, f(x, y, z) or g(x, y, z), due to the nonlinear artifact production mechanism, and their interaction with the reconstruction process. Thus, the method 94 includes producing a mapping function, τ, which performs nonlinear mapping on ρ(x, y, z) to generate the final metal artifact correction signal 96, ε(x, y, z) as described in the following equation $$\epsilon(x,y,z)=\tau[\rho(x,y,z)] \quad (5).$$

In certain embodiments, the nonlinear mapping function, τ, may also be used to suppress the residual signal of the bony structure or the iodine contrast enhanced anatomies. For example, in some embodiments, frequency based filtering may be used in the mapping function, τ. If the intermediate images included contamination by photon starvation artifacts, the noise components of these photon starvation artifacts may also be removed via the frequency based filtering. In certain embodiments, the filter for frequency based filtering may be anisotropic. The conditioning of the metal artifact signal 72 may include all or only some of the acts described above for method 94.

Technical effects of the disclosed embodiments include utilizing a projection-space correction approach to compensate for metal artifacts. The approach utilizes images or sets of images at two different energy spectrums or energy levels and extracting the metal artifact correction signal 72, 96 for correcting the original reconstructed images 70 or scans via image processing manipulations, while minimizing the impact on residual signals from normal anatomies such as the soft tissue and bones. In addition, the projection-space correction approach takes into account the difference in Hounsfield units (HU) of the images across different X-ray tube voltages, the selection of data to be used for generating the artifact signature, motion, and other factors.

This written description uses examples to disclose the present subject matter, including the best mode, and also to enable any person skilled in the art to practice the present approaches, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method comprising:
acquiring a first dataset at a first energy spectrum and a second dataset at a second energy spectrum;
extracting a metal artifact correction signal using the first dataset and the second dataset or using a first reconstructed image and a second reconstructed image generated respectively from the first dataset and the second dataset; and
performing metal artifact correction on the reconstructed images using the metal artifact correction signal to generate corrected images, wherein the first energy spectrum and second energy spectrum comprise different tube voltages, different filtration levels, different filtration types, or a combination thereof.

2. The method of claim 1, comprising performing metal artifact correction on the second reconstructed image using the metal artifact correction signal to generate a second corrected image.

3. The method of claim 1, comprising registering the first reconstructed image and second reconstructed image to each other to correct for motion prior to extracting the metal artifact correction signal.

4. The method of claim 1, comprising generating a weighting map to determine an amount of correction for the first reconstructed image or the second reconstructed image, wherein the weighting map is based on a distance from a source of metal-induced error.

5. The method of claim 4, comprising weighting the metal artifact correction signal with the weighting map to generate a weighted metal artifact correction signal.

6. The method of claim 5, comprising applying adaptive image-space filtering to the weighted metal artifact correction signal to reduce noise.

7. The method of claim 6, wherein applying adaptive image-space filtering comprises applying an anisotropic diffusion filter to the weighted metal artifact correction signal.

8. The method of claim 1, comprising performing nonlinear mapping on the metal artifact correction signal via a nonlinear mapping function to generate a final metal artifact correction signal.

9. The method of claim 8, wherein the nonlinear mapping function utilizes frequency based filtering to remove noise from photon starvation artifacts.

10. The method of claim 1, comprising determining a first optimal energy spectrum for the first energy spectrum and a second optimal energy spectrum for the second optimal energy spectrum for performing a computed tomography scan to obtain the first and second images, wherein determining the optimal first and second energy spectra is based on a scout scan image.

11. The method of claim 1, comprising:
determining if the first corrected image needs further metal artifact correction; and
if the first corrected image needs further metal artifact correction, performing iterative metal artifact correction using the metal artifact correction signal until no further metal artifact correction is needed.

12. One or more non-transitory computer-readable media encoding one or more processor-executable routines, wherein the one or more routines, when executed by a processor, cause acts to be performed comprising:
acquiring a first dataset at a first energy spectrum and a second dataset at a second energy spectrum;
extracting a metal artifact correction signal using the first dataset and the second dataset or using a first reconstructed image and a second reconstructed image generated respectively from the first dataset and the second dataset; and
performing metal artifact correction on the first reconstructed image using the metal artifact correction signal to generate a first corrected image, wherein the first energy spectrum and second energy spectrum comprise different tube voltages, different filtration levels, different filtration types, or a combination thereof.

13. The one or more non-transitory computer-readable media of claim 12, wherein the one or more routines, when executed by the processor, cause further acts to be performed comprising:
performing metal artifact correction on the second reconstructed image using the metal artifact correction signal to generate a second corrected image.

14. The one or more non-transitory computer-readable media of claim 12, wherein the one or more routines, when executed by the processor, cause further acts to be performed comprising:
registering the first reconstructed image and second reconstructed image to each other to correct for motion prior to extracting the metal artifact construction signal.

15. The one or more non-transitory computer-readable media of claim 12, wherein the one or more routines, when executed by the processor, cause further acts to be performed comprising:
generating a weighting map to determine an amount of correction for the first reconstructed image or the second reconstructed image, wherein the weighting map is based on a distance from a source of metal-induced error.

16. The one or more non-transitory computer-readable media of claim 15, wherein the one or more routines, when executed by the processor, cause further acts to be performed comprising:
weighting the metal artifact correction signal with the weighting map to generate a weighted metal artifact correction signal.

17. The one or more non-transitory computer-readable media of claim 12, wherein the one or more routines, when executed by the processor, cause further acts to be performed comprising:
performing nonlinear mapping on the metal artifact correction signal via a nonlinear mapping function to generate a final metal artifact correction signal.

18. The one or more non-transitory computer-readable media of claim 12, wherein the one or more routines, when executed by the processor, cause further acts to be performed comprising:
determining if the first corrected image needs further metal artifact correction; and
if the first corrected image needs further metal artifact correction, performing iterative metal artifact correction using the metal artifact correction signal until no further metal artifact correction is needed.

19. A system comprising:
a memory structure encoding one or more processor-executable routines, wherein the routines, when executed cause acts to be performed comprising:
acquiring a first dataset at a first energy spectrum and a second dataset at a second energy spectrum;
extracting a metal artifact correction signal using the first dataset and the second dataset or using a first reconstructed image and a second reconstructed image generated respectively from the first dataset and the second dataset;
performing nonlinear mapping on the metal artifact correction signal via a nonlinear mapping function to generate a final metal artifact correction signal;
performing metal artifact correction on the first reconstructed image using the final metal artifact correction signal to generate a first corrected image; and
a processing component configured to access and execute the one or more routines encoded by the memory structure.

20. The system of claim 19, wherein the routines, when executed by the processor, cause further acts to be performed comprising:
performing metal artifact correction on the second reconstructed image using the final metal artifact correction signal to generate a second corrected image.

21. The system of claim 19, wherein the routines, when executed by the processor, cause further acts to be performed comprising:
registering the first reconstructed image and second reconstructed image to each other to correct for motion prior to extracting the metal artifact construction signal.

22. The system of claim 19, wherein the routines, when executed by the processor, cause further acts to be performed comprising:
generating a weighting map to determine an amount of correction for the first reconstructed image or the second reconstructed image, wherein the weighting map is based on a distance from a source of metal-induced error;
weighting the metal artifact correction signal with the weighting map to generate a weighted metal artifact correction signal; and
performing nonlinear mapping on the weighted metal artifact correction signal via the nonlinear mapping function to generate the final metal artifact correction signal.

* * * * *